United States Patent [19]

Jariwala

[11] 4,091,204

[45] May 23, 1978

[54] PROCESS FOR RECOVERING LINCOMYCIN FROM FERMENTATION BEER

[75] Inventor: Sharad L. Jariwala, Kalamazoo, Mich.

[73] Assignee: The Upjohn Company, Kalamazoo, Mich.

[21] Appl. No.: 726,350

[22] Filed: Sep. 24, 1976

Related U.S. Application Data

[63] Continuation of Ser. No. 534,665, Dec. 20, 1974, abandoned.

[51] Int. Cl.$^2$ .............................................. C12D 9/00
[52] U.S. Cl. ................................... 536/11; 195/66 R; 195/80 R; 203/63
[58] Field of Search ............. 195/66 R, 104, 98, 80 R; 260/210 R; 203/63

[56] References Cited

U.S. PATENT DOCUMENTS

| | | | |
|---|---|---|---|
| 2,602,045 | 7/1952 | Hodge | 203/63 |
| 2,929,150 | 3/1960 | Johnston | 195/66 R |
| 3,086,912 | 4/1963 | Bergy et al. | 195/80 R |
| 3,616,244 | 10/1971 | Argoudelis et al. | 260/210 R |

*Primary Examiner*—Alvin E. Tanenholtz
*Attorney, Agent, or Firm*—Martin B. Barancik

[57] ABSTRACT

A dry-down method for partially recovering biologically active substance from fermentation beers.

6 Claims, No Drawings

PROCESS FOR RECOVERING LINCOMYCIN FROM FERMENTATION BEER

This is a continuation of pending application Ser. No. 534,665, filed Dec. 20, 1974 and now abandoned.

BRIEF DESCRIPTION OF THE PRIOR ART

Biologically active fermentation elaboration products were recovered initially by rather simple methods of solvent extraction and distillation. Presently, one of the favored modes of initial recovery steps is the separation of the desired product from the fermentation beer components and elaboration by-products through the use of a selective sorbent, often an ion exchange column. In such a process, large volumes of liquids are utilized with concomitant physical losses of end product. Additionally, the cost of the sorbent itself, as well as the sequential steps of loading, eluting and regenerating the sorbent with the attendant man-hours involved, are serious disadvantages. Furthermore, when using the sorption method, the recovery process is generally continued until a primary extraction of the desired product is executed.

A new method for recovering fermentation elaboration products having biological activity has been discovered.

BRIEF SUMMARY OF THE INVENTION

Accordingly there is disclosed a novel process for partially recovering biologically active substances from fermentation beer which comprises adding to the said fermentation beer an inert relatively non-volatile, relatively immiscible organic oil to obtain an admixture which will be fluid and pumpable after removal of water, azeotroping off the water by heating at a temperature which maintains the biological stability of the active substance, and separating the organic oil from the dried fermentation beer solids.

This method should not involve the substantial volumes and costly man hours of present-day methods. The apparatus used is generally much simpler than earlier used apparatus. The process provides a flexibility to fermentation recovery process apparatus and timing not heretofore observed.

Methods similar to the ones disclosed here have been utilized in the treatment of sewage sludge, see U.S. Pat. No. 3,251,398. However, there is no mention of using this method for the recovery of fermentation products having biological activity, even though a similar process is being used to treat fermentation plant waste at Eli Lilly's Clinton, Indiana fermentation plant, Chemical Week, May 9, 1973.

DETAILED DESCRIPTION OF THE INVENTION

The fermentation beers which can be treated by the methods of this invention include any beer which is of sufficient consistency to readily lose its water through volatilization. Examples of beers which can be used in this method of this invention include lincomycin, neomycin, erythromycin and protease fermentation beers. The biologically active substance to be recovered should generally be within the beer itself rather than located inside the mycelia.

The term "biologically active substance" includes antibiotics, relatively heat stable enzymes and yeast proteins and any other substance which exerts a biological change or influences the biochemical processes of mammals. Exemplary antibiotics include novobiocin, tetracyclines, erythromycin, lincomycin and chloramphenicol. Examples of enzymes which can be recovered by this method include protease, glucose isomerase, and high temperature amylases.

The organic oil which is added to the fermentation beer is an inert, relatively non-volatile, relatively immiscible oil or other non-volatile oil-like materials or non-volatile fractions thereof. Typical of these are petroleum oil, lubricating oils, fuel oils, glycerine, glycols, alcohols, and so forth. The quantity of oil is not critical but it should generally be used in a quantity sufficient to give a fluid pumpable mixture even with the mixture's water content removed. The term "fluid" is intended to be synonymous with "liquid", i.e., taking the shape of the container. Thus, the term "organic oil" will also include heavy, viscous fluids which are pumpable for purposes such as heater transfer. The actual quantity of oil will depend upon the physical characteristics of the beer and oil. Generally a range of about one to about five volume parts of oil to volumes parts of beer can be used. The fermentation broth can be generally used as it is found in the vat, i.e., the whole beer. Occasionally, slight screening to remove agglomerated chunks may be necessary.

In choosing on organic oil to add to the fermentation beer, it is preferred to choose a chemical in which the desired biological substance is preferentially soluble. In this manner, a partical separation of the biological substance from the solid fermentation material is achieved upon dehydration. For example, when lincomycin is being recovered by this method, n-butanol is a preferred solvent since it meets the other criteria of the organic oil and the lincomycin is preferentially soluble in n-butanol.

The temperature at which the azeotroping occurs is determined by the organic oil employed, the pressure, and the biological substance involved. The pressure and organic oil used must be such that the activity of the biological substance is essentially unaltered and can, at least, meet minimum standards for the material. Choice of these parameters is within the knowledge and skill of the average practitioner.

After the volatilization occurs, the organic oil is separated from the essentially dry fermentation residue slurry by any convenient means. Centrifugation is operable and mere decantation can suffice at times. Pressing can be employed to separate the residue from the extra oil, if the organic solvent is of sufficient viscosity. When an undue amount of oil occludes to the residue, it may be readily removed by washing.

The biologically active substance can be readily precipitated and purified by standard means known in the art, when the organic oil contains the substance. Alternatively, if the active substance is still in the dried fermantation residue, the residue is extracted with a solvent which solubilizes the desired substance to a greater extent than the remainder of the residue. However, the desired substance need not be extracted immediately. Because the fermentation residue has been substantially dehydrated, the risk of degrading the desired substance is reduced substantially. Consequently, the dried residue can be stored for lengthy periods of time prior to extraction of the desired substance. This provides a flexibility of production planning and equipment usage not heretofore obtained in fermentation processing. The fluidity of the slurry allows for easy handling during this period as well as during the entire drying procedure. Consequently, no special equipment is generally necessary during the procedure.

The choice of extractant employed in the recovery of the substance from the dried residue is dependent upon the characteristics of the substance and by-products. Generally, the extractant used commonly in other recovery procedures can also be empolyed in this invention. Care should be taken so that the finely divided dried solids do not agglomerate in this procedure, thus lowering the final yield of extracted material.

The final yields of the desired substance compare favorably with the common methods of recovery and in some instances can be significantly higher. Savings in the cost of recovering the desired substance can also be achieved.

Following are specific examples illustrating this invention. These examples are not intended to limit but merely to exemplify the invention.

EXAMPLE 1

Fermentation beer prepared according to the procedure of U.S. Pat. No. 3,086,912 is harvested. A five gallon whole beer sample is admixed with five gallons of Isopar ®, a Cg petroleum distillate. Drying is conducted in a single effect evaporator at 180° F. for a period of 6 hours. Isopar ® is obtained from Exxon.

The lincomycin is extracted from the dried solids in a batch-wise manner. Ten grams of dried solids are extracted with 50 ml. of a n-butanol water solution which has been made alkaline by the addition of sodium hydroxide. The solids are then filtered and washed. The washings are added to the extract.

The extract is concentrated to a lincomycin base concentration of 100-125 g/l. The pH is adjusted to 5 with HCl. The concentrate is decolorized with Darco ®. The decolorized material is then reextracted with water. The pH of the aqueous phase is raised to 10 with NaOH and the lincomycin base is back extracted into methylene chloride. The methylene chloride phase is concentrated and during this concentration step a change is made in the solvent to n-butanol. Lincomycin is crystallized out as lincomycin hydrochloride by the addition of HCl.

Approximately 85% of the lincomycin in the whole beer is found in the dried solids. The overall yield from dried solids to crystalline material in 74.8%.

EXAMPLE 2

Fermentation beer prepared as in Example 1 is harvested. A two liter whole beer sample is admixed with two liters of n-butanol. Drying is conducted in a single effect evaporator at approximately 150° F. for a period of 6 hours.

Lincomycin is quantitatively extracted into n-butanol by adding sodium hydroxide solution to convert lincomycin to the free base form. The extraction is done in a batch-wise manner. The spent solids residue is filtered and washed after each extraction and the washings are added to the extract.

The extract is concentrated to a lincomycin base concentration of 100-125 g/l. The pH is adjusted to 5 with HCl. The concentrate is decolorized with Darco ®. The decolorized material is then re-extracted with water. The pH of the aqueous phase is raised to 10 with NaOH and the lincomycin base is back-extracted into methylene chloride. The methylene chloride phase is concentrated and during the concentration step a change is made in the solvent to n-butanol. Lincomycin is crystallized out as lincomycin hydrochloride by the addition of HCl. The overall yield from lincomycin whole beer to crystalline material is 80%.

It should be noted that the term "immiscible" used throughout the specification and claims refers to water immiscibility.

I claim:

1. A method for partially recovering dried lincomycin from whole or screened whole fermentation beer which comprises
    a. adding to the said whole or screened whole fermentation beer an inert, relatively non-volatile, relatively water immiscible organic oil to obtain an admixture which is fluid and pumpable after removal of water,
    b. azeotroping off the water by heating at a temperature which maintains the biological stability of lincomycin, and
    c. separating the organic oil from the dried fermentation beer solids.

2. A method in accordance with claim 1 wherein the fermentation beer is whole beer.

3. A method in accordance with claim 1 wherein the fermentation beer is screened whole beer.

4. A method for partially recovering lincomycin form whole or screened whole fermentation beer which comprises
    a. adding to the said fermantation beer n-butanol to obtain an admixture which is fluid and pumpable after removal of water,
    b. azeotroping off the water by heating at a temperature which maintains the biological stability of lincomycin, and
    c. separating n-butanol from the dried fermentation beer solids.

5. A method in accordance with claim 4 wherein the fermentation beer is whole beer.

6. A method in accordance with claim 4 wherein the fermentation beer is screened whole beer.

* * * * *

UNITED STATES PATENT AND TRADEMARK OFFICE
CERTIFICATE OF CORRECTION

PATENT NO. : 4,091,204
DATED : May 23, 1978
INVENTOR(S) : Sharad J. Jariwala

It is certified that error appears in the above—identified patent and that said Letters Patent is hereby corrected as shown below:

Column 4, line 40; change "form" to --from--.

Column 4, line 43; change "fermantation beer" to --whole or screened whole fermentation beer--.

Signed and Sealed this

Twenty-second Day of July 1980

[SEAL]

Attest:

SIDNEY A. DIAMOND

Attesting Officer     Commissioner of Patents and Trademarks